United States Patent [19]

Chapura et al.

[11] Patent Number: 4,786,502

[45] Date of Patent: Nov. 22, 1988

[54] PALATABLE SOLID PHARMACEUTICAL COMPOSITIONS

[75] Inventors: Francis B. Chapura, Hamilton; Charles W. Bishop, Cincinnati; Kenneth Charak, Fairfield; Phillip F. Pflaumer, Hamilton; David L. Suter, Fairfield, all of Ohio

[73] Assignee: The Procter & Gamble Company, Cincinnati, Ohio

[21] Appl. No.: 916,062

[22] Filed: Oct. 6, 1986

[51] Int. Cl.$^4$ .................... A61K 33/08; A61K 33/10
[52] U.S. Cl. ............................. 424/441; 424/484
[58] Field of Search ........................ 424/441, 484

[56] References Cited

U.S. PATENT DOCUMENTS

| | | | |
|---|---|---|---|
| 3,037,911 | 6/1962 | Stoyle et al. | 424/441 |
| 3,253,988 | 5/1966 | Scott | 167/55 |
| 3,767,801 | 10/1973 | Tuma et al. | 424/230 |
| 4,230,693 | 10/1980 | Izzo et al. | 424/156 |
| 4,327,076 | 4/1982 | Puglia et al. | 424/38 |
| 4,327,077 | 4/1982 | Puglia et al. | 424/38 |
| 4,533,543 | 8/1985 | Morris et al. | 424/38 |
| 4,545,989 | 10/1985 | Becker et al. | 424/154 |
| 4,581,381 | 4/1986 | Morris et al. | 514/819 |
| 4,588,604 | 5/1986 | Baker et al. | 426/601 |
| 4,594,259 | 6/1986 | Baker et al. | 426/613 |
| 4,609,543 | 9/1986 | Morris et al. | 424/38 |
| 4,650,665 | 3/1987 | Kronenthal et al. | 424/484 X |

FOREIGN PATENT DOCUMENTS 4023285 6/1974 Japan ......................... 423/5

OTHER PUBLICATIONS

Gutteridge, M. C., et al., "The *in vitro* Neutralisation Characteristics of Oleaginous Antacid Suspensions", 32 *J. of Pharmacy and Pharmacology*, Suppl. 63P (1980).

Bochev B., et al., "Comparative *in vitro* Investigations on the Release of Drugs from Suppository Bases", 20 *Farmatsiya (Sofia)* 22–27 (1970).

*Primary Examiner*—Nancy A. B. Swisher
*Attorney, Agent, or Firm*—David L. Suter; Richard C. Witte; Kim William Zerby

[57] ABSTRACT

Lipid-containing, molded pharmaceutical compositions, comprising:

(a) from about 10% to about 50% of a lipid material having a melting point of from about 26° C. to about 37° C.;
(b) from about 10% to about 50% of a particulate dispersant material;
(c) from about 0.1% to about 3% of an emulsifier; and
(d) a safe and effective amount of a pharmaceutical active material;

wherein the particulate materials in said composition have a mean particle size of from about 4 microns to about 10 microns, with less than about 10% of the particulates greater than about 30 microns in size. Preferably, the measured viscosity of the compositions is less than about 10,000 cps at about 40° C.

16 Claims, No Drawings

PALATABLE SOLID PHARMACEUTICAL COMPOSITIONS

BACKGROUND OF THE INVENTION

This invention relates to palatable solid pharmaceutical compositions useful in humans and other animals. In particular, it relates to highly efficacious compositions comprising a pharmaceutical active in a lipid-containing matrix. Preferred compositions further relate to highly palatable tablets, which are chewable or liquify in the mouth, useful for the treatment of gastrointestinal disorders.

Pharmaceutical compositions may be produced in a variety of dosage forms, depending upon the desired route of administration of the active material. Oral dosage forms, for example, include such solid compositions as tablets, capsules, granules and bulk powders, and such liquid compositions as solutions, emulsions, and suspensions. The particular dosage form utilized may, of course, depend upon such factors as the solubility and chemical reactivity of the pharmaceutical active. Further, the dosage form may be selected so as to optimize delivery of the pharmaceutical active and/or consumer acceptability of the composition.

Tablet compositions offer many advantages, including ease of product handling, chemical and physical stability, portability (in particular, allowing ready availability to the consumer when needed), aesthetic acceptability, and dosage precision, (i.e., ensuring consistent and accurate doses of the pharmaceutical active). However, liquid formulations may offer advantages in the treatment of certain disorders, such as disorders of the upper gastrointestinal tract, wherein delivery of an active material dissolved or dispersed in a liquid ensures rapid and complete delivery to the afflicted area. In an effort to obtain the therapeutic advantages associated with liquid formulations as well as the broad advantages associated with solids, many chewable tablet formulations have been developed and described in the pharmaceutical literature. See, for example, L. Lachman, et al., *The Theory and Practice of Industrial Pharmacy* (2nd Ed., 1976).

Many such compositions are antacids, for the treatment of gastric hyperacidity and related disorders. Many antacid compositions in liquid form are quite effective due to the ready availability of the antacid active material (which is typically water-insoluble) suspended in a liquid vehicle. There are also many solid antacid formulations, typically chewable tablets, which are designed to deliver small particles of antacid active to the stomach after chewing of the tablet.

Chewable tablets, such as antacid tablets, often contain high levels of mannitol or similar binders as well as methylcellulose, glycine, or other binding agents. Other chewable tablets are described in the literature containing fatty materials. See, for example, U.S. Pat. No. 4,230,693, Izzo, et al., issued Oct. 28, 1980, U.S. Pat. No. 4,327,076, Puglia, et al., issued Apr. 27, 1982, U.S. Pat. No. 4,327,077, Puglia, et al., issued Apr. 27, 1982, U.S. Pat. No. 4,533,543, Morris, et al., issued Aug. 6, 1985, and U.S. Pat. No. 4,581,381, Morris, et al., issued Apr. 8, 1986.

Many such solid antacid formulations fail to offer equivalent efficacy to liquid antacid compositions, for a variety of reasons. For example, the tablets may be incompletely chewed due to poor palatability of the composition. This problem is particularly acute with antacids, since the active materials in these products often have a metallic flavor and an astringent, chalky mouth feel. Such compositions may also have a gummy texture, and are subject to "taste fatigue", i.e., the composition is perceived to be less palatable after ingestion of multiple doses. Further, the binders and other materials used in such chewable tablets may prevent rapid and effective delivery of active materials to the stomach.

It has been found that tablet formulations containing selected lipid materials, emulsifiers and particulate materials are highly palatable and effective compositions for the delivery of pharmaceutical active materials. Such compositions afford better taste, mouth feel, and storage stability than compositions known in the art. For example, such compositions containing selected materials with selected particle sizes, and formulated to have a selected product viscosity, afford improved palatability when compared to other lipid containing compositions.

SUMMARY OF THE INVENTION

The present invention provides lipid-containing, molded pharmaceutical compositions, comprising:
 (a) from about 10% to about 50% of a lipid material having a melting point of from about 26° C. to about 37° C.;
 (b) from about 10% to about 50% of a particulate dispersant material;
 (c) from about 0.1% to about 3% of an emulsifier; and
 (d) a safe and effective amount of a pharmaceutical active material;

wherein the particulate materials in said composition have a mean particle size of from about 4 microns to about 10 microns, with less than about 10% of said particulates greater than about 30 microns in size. Preferably, the measured viscosity of said composition is less than about 10,000 cps at about 40° C.

Among the preferred lipid-containing compositions of this invention are chewable tablets useful for the treatment of upper gastrointestinal disorders, such as an antacid composition containing from about 10% to 65% of an acid neutralizing material. The present invention also provides coated unit dosage compositions which comprise the lipid-containing solid compositions of this invention coated with a solid coating material.

DESCRIPTION OF THE INVENTION

The compositions of the present invention contain a pharmaceutical active material in a vehicle containing a lipid base material, a dispersant material and an emulsifier. In addition, the compositions of the present invention may contain optional pharmaceutically-acceptable components which may modify their physical characteristics and/or therapeutic effects. All components of the present compositions must, of course, be pharmaceutically-acceptable. As used herein, a "pharmaceutically-acceptable" component is one which is suitable for use with humans and/or other animals without undue adverse side effects (such as toxicity, irritation and allergic response) commensurate with a reasonable benefit/risk ratio.

The present invention provides lipid-containing, molded pharmaceutical compositions, comprising:
 (a) from about 10% to about 50% of a lipid material having a melting point of from about 26° C. to about 37° C.;

(b) from about 10% to about 50% of a particulate dispersant material;

(c) from about 0.1% to about 3% of an emulsifier; and (d) a safe and effective amount of a pharmaceutical active material;

wherein the particulate materials in said composition have a mean particle size of from about 4 microns to about 10 microns, with less than about 10% of said particulates greater than about 30 microns in size. Preferably, the measured viscosity of said composition is less than about 10,000 cps at about 40° C. Except as otherwise stated, all percentages set forth herein are by weight of total composition.

Further, as used herein, the term "safe and effective amount" refers to the quantity of a component which is sufficient to yield a desired therapeutic response without undue adverse side effects (such as toxicity, irritation or allergic response) commensurate with a reasonable benefit/risk ratio when used in the manner of this invention. The specific "safe and effective amount" will, obviously, vary with such factors as the particular condition that is being treated, the severity of the condition, the duration of the treatment, the physical condition of the patient, the nature of concurrent therapy (if any), and the specific formulation and optional components employed.

Preferably, the lipid base material is present in the present compositions at a level of from about 20% to about 40%, more preferably from about 25% to about 40%. Also preferably, the dispersant material is present at a level of from about 20% to about 40%, more preferably from about 20% to about 35%. The emulsifier is preferably present at a level of from about 0.5% to about 2%, more preferably from about 0.6% to about 1.5%. Specific components, and optional materials useful in these chewable tablet compositions are further described below.

These compositions may be provided in unit-dosage form, as molded tablets. Molded tablets are produced by forming a liquid product mass, i.e., by melting the fatty carrier materials and admixing the other components, followed by pouring into tablet-form molds, and cooling to a solid state. Although these compositions may be swallowed whole or in part without chewing, the present compositions are preferably comprised so as to facilitate chewing and/or melting in the mouth. The present compositions thereby facilitate dispersion of the pharmaceutical active material in saliva and (after swallowing, ultimately) in the gastric fluids of the stomach.

Essential Components

As described above, the present chewable tablet compositions contain four essential components: a lipid base material, a dispersant material, a nonionic emulsifier material, and a pharmaceutical active material. These compositions may also contain optional components, such as other emulsifiers, tempering aids, flavorants and colorants.

Lipid Material:

The compositions of the invention contain one or more materials, (herein individually and in mixtures referred to as "lipid materials") that are substantially water-insoluble, inert, pharmaceutically-acceptable hydrocarbon fats or oils, or their derivatives, or mixtures thereof. The lipid materials useful herein preferably have a melting point of from about 26° C. (80° F.) to about 37° C. (99° F.), preferably from about 32° C. (90° F.) to about 35° C. (95° F.), more preferably about 33° C. (91° F.). (As used herein "melting point" refers to the capillary melting point, at which essentially all of the fat is in a liquid state.) The particular lipid material employed may be selected in order to obtain desired product characteristics. These characteristics include such factors as rheology (mouth feel), appearance, flavor and compatibility with the pharmaceutical active.

Among the lipid materials useful herein are those which are commercially available and commonly used in confectionery and other food products. Such lipid materials include, for example, cocoa butter, hydrogenated tallow, hydrogenated vegetable oils, and derivatives and mixtures thereof. Hydrogenated vegetable oils (such as hydrogenated palm kernel oil), cocoa butter, and cocoa butter substitutes are among the preferred useful lipid materials. Lipid materials among those useful in this invention are described in the following documents, all incorporated by reference herein: U.S. Pat. No. 2,903,363, Farr, issued Sept. 8, 1959; British Patent Specification No. 827,176, Best et al., published Feb. 3, 1960; U.S. Pat. No. 3,012,891, Best et al., issued Dec. 12, 1961; U.S. Pat. No. 3,093,480, Arnold, issued June 11, 1963; U.S. Pat. No. 3,492,130, Harwood, issued Jan. 27, 1970; U.S. Pat. No. RE 28,737, Yetter reissued Mar. 16, 1976; European Patent Application No. 23,062, Cotton et al., published Jan. 28, 1981; U.S. Pat. No. 4,276,322, Padley et al., issued June 30, 1981; U.S. Pat. No. 4,283,436, Soeters et al., issued Aug. 31, 1981; U.S. Pat. No. 4,364,868, Hargreaves, issued Dec. 21, 1982; and U.S. Pat. No. 4,581,381, Morris et al., issued Apr. 8, 1986; and U.S. Pat. No. 4,594,259, Baker et al., issued June 10, 1986.

Particularly preferred lipid materials are those that melt sharply at about 33° C. (91° F.). Such fats which melt "sharply" are those with melting profiles similar to cocoa butter, which is a solid at ambient temperatures, but is entirely liquid at a point just below mouth temperature (approximately 34° C.).

A commercially available material having such a preferred melting profile is Hydrokote, SP1, manufactured by Capital Cities Products Co. (Division of Stokely-VanCamp, Inc.). The solid fat index of this lipid material shows that the fat melts sharply at just below 34° C.; being about 65% to 69% solid at about 21° C. (70° F.), about 52% to 56% solid at about 26° C. (80° F.), and less than about 1% solid at about 33.5° C. (92° F.).

Another particularly preferred lipid material is described in U.S. Pat. No. 4,594,259, Baker et al., issued June 10, 1986. Solid pharmaceutical compositions containing these particularly preferred materials are described in U.S. patent application Ser. No. 916,061, filed Oct. 6, 1986. Such particularly preferred compositions contain one or more materials, herein "lipid base materials", which together with all other mono-, di- and triglycerides (if any) in the compositions form the "lipid component" of the chewable tablet compositions. The lipid component of the present composition thus preferably contains certain key triglycerides: saturated-oleic-saturated ("SOS"), saturated-unsaturated-saturated ("SUU"), unsaturated-unsaturated-unsaturated ("UUU"), saturated-lineolic-saturated ("SLS"), saturated-saturated-oleic ("SSO"), and saturated-saturated-saturated ("SSS") triglycerides, i.e., referring to the chemical structure of the fatty acid moiety of each glyceride in the key triglyceride. As used herein, "S" refers to the stearic ("St") or palmitic ("P") fatty acid residues of the glyceride molecule and ("U") refers to the oleic ("O") or linoleic ("L") fatty acid residues of the glyceride molecule.

Specifically, the lipid component of such particularly preferred composition contains at least about 70% of SOS triglycerides, and from about 4% to about 20% of combined SUU/UUU/SLS triglycerides, where the St:P weight ratio is about 0.8 or less. (These percentages are by weight of the lipid component, not by weight of total composition.) Preferably the lipid component contains about 8% or less of SLS triglycerides, about 9.5% or less of SSO triglycerides, about 2.5% or less of SSS triglycerides, and about 4% or less of other triglycerides. The lipid component of the present invention preferably is comprised entirely of a fat having a low St:P ratio (about 0.2 or less). A POP fat is particularly preferred. A preferred source of POP fat is through a triple stage solvent fractionation of palm oil. This process is described in U.S. Pat. No. 4,588,604, Baker et al., issued May 13, 1986 (incorporated by reference herein).

Dispersant Material:

The compositions of this invention also contain a hydrophilic material, herein "dispersant material", which serves to aid dispersion of the pharmaceutical active and other materials of the composition in the mouth and/or stomach. Many dispersants among those useful herein are known in the pharmaceutical arts. Dispersant materials among those useful herein include sugars (such as sucrose, mannitol, sorbitol, dextrose, maltose, and lactose), starches and starch derivatives (such as corn starch and maltodextrin), microcrystalline cellulose, and mixtures thereof. Among the preferred dispersant materials useful herein are sucrose, sorbitol, mannitol, and mixtures thereof.

Emulsifier Material:

The compositions of this invention also contain one or more emulsification materials (herein individually and in mixtures referred to as "emulsifiers"). Emulsifiers may be characterized by their hydrophilic/lipophilic behavior. This behavior can be numerically expressed for a given emulsifier by its hydrophilic-lipophilic balance (HLB). The HLB value of an emulsifier can be determined experimentally or computed (particularly for polyoxyethylene ethers) from its structural formula. In general, emulsifiers with high HLB values are more hydrophilic, and tend to favor formation of oil-in-water emulsions, as opposed to emulsifiers with lower HLB values.

Among the emulsifiers useful herein are the alkyl aryl sulfonates, alkyl sulfates, sulfonated amides and amines, sulfated and sulfonated esters and ethers, alkyl sulfonates, polyethoxylated esters, mono- and diglycerides, diacetyl tartaric esters of monoglycerides, polyglycerol esters, sorbitan esters and ethoxylates, lactylated esters, propylene glycol esters, sucrose esters, and mixtures thereof.

Many such emulsifiers are known in the pharmaceutical arts. See, for example, M. Riegler, "Emulsions", *The Theory and Practice of Industrial Pharmacy* (L. Lachman, et al., ed. 1976), incorporated by reference herein. Emulsifiers among those useful herein are also described in *McCutcheon's Emulsifiers and Detergents, North American Edition* (1983), incorporated by reference herein.

Preferably the emulsifier used in the present compositions includes a "low HLB emulsifier", i.e., an emulsifier having an HLB of from about 4 to about 10, more preferably from about 6 to about 10. Such low HLB emulsifiers are preferably included at a level of from about 0.1% to about 1%, more preferably from about 0.1% to about 0.5%. Also preferably, the present compositions are essentially free (e.g., containing less than about 0.1%) of emulsifiers having HLB values less than about 4.

Many low HLB emulsifiers are commercially available. Such emulsifiers among those useful herein include: Caprol 6G2S (hexaglycerol distearate), manufactured by Capital Cities Products Co.; Artodan (sodium stearoyl lactylates), manufactured by Grinsted Products; Myvatem 30 (monoglyceride diacetyl tartaric acid esters), manufactured by Eastman Chemical Products, Inc.; Polyaldo HGDS (hexaglycerol distearate) and Polyaldo TGMS (triglycerol monostearate), manufactured by Glyco Inc.; and Span 60 (sorbitan monostearate) and Span 80 (sorbitan monooleate), manufactured by ICI Americas, Inc.

The compositions of this invention also preferably contain one or more high HLB emulsifiers as a part of the emulsifier component. In particular, the present compositions preferably contain from about 0.1% to about 3%, more preferably from about 0.5% to about 2%, more preferably from about 0.6% to about 1.5% of a nonionic emulsifier having an HLB of at least about 10. Preferably, the high HLB emulsifier has an HLB of at least about 11. Many such nonionic emulsifiers are commercially available. Such emulsifiers include, for example: Caprol PGE860 (Decaglycerol mono-dioleate), manufactured by Capital Cities Products Co.; Hodag PSMS-20 (polyoxyethylene sorbitan) and Hodag SVO-9 (polyoxyethylene sorbitan 20 monooleate), manufactured by Hodag Chemical Corp.; Liposorb L-20 (polysorbate 20), Liposorb 0-20 (polysorbate 80), and Liposorb S-20 (polysorbate 60), manufactured by Lipo Chemicals, Inc.; Pluronic F69 (block copolymer of propylene oxide and ethylene oxide), manufactured by BASF Wyandotte Corp.; Santone 8-1-S (polyglycerol esters of fatty acids), manufactured by Durkee Industrial Foods Group of SCM Corp.; and Tween 20 (polyoxyethylene 20 sorbitan monolaurate), Tween 60 (polyoxyethylene 20 sorbitan monostearate), Tween 80 (polyoxyethylene 20 sorbitan tristerate, polysorbate 65) and Myrj 52 (polyoxyl 40 stearate), manufactured by ICI Americas, Inc.

The average HLB of all emulsifiers incorporated in the present compositions is preferably at least about 8, more preferably at least about 10. As used herein, the term "average HLB" refers to the weighed average of the HLB of all emulsifiers in the composition; i.e., $$\text{total } HLB = \frac{HLB_1 \times \text{Wt \% } E_1 + HLB_2 \times \text{Wt \% } E_2 + \ldots HLB_n \times \text{Wt \% } E_n}{\text{Wt \% } E_1 + \text{Wt \% } E_2 + \ldots \text{Wt \% } E_n}$$

wherein the composition contains "n" number of emulsifiers. The use of such high HLB emulsifiers to increase the efficacy of lipid-containing compositions is described in U.S. patent application Ser. No. 916,065, filed Oct. 6, 1986 (incorporated by reference herein).

Pharmaceutical Active Material:

The present compositions also contains a "pharmaceutical active material", i.e., a material which is intended to have a physiologic effect on the human or lower animal to whom the composition is administered. Pharmaceutical active materials particularly useful in the chewable tablet formulations of this invention include those actives which become bioavailable and/or have their site of action in the mouth or stomach. The rapid dispersion of such active materials in the saliva, as afforded by the present chewable tablets, is particularly advantageous. Among such active materials are the analgesics, such as aspirin and acetaminophen, and materials useful in the treatment of gastrointestinal disorders.

Among the pharmaceutical active materials particularly useful in the compositions of this invention are the bismuth salts and the metallic antacid salts. Such bismuth salts include, for example, bismuth aluminate, bismuth citrate, bismuth nitrate, bismuth subcarbonate, bismuth subgalate, bismuth subsalicylate, and mixtures thereof. A particularly preferred bismuth salt is bismuth subsalicylate. Metallic antacid salts useful herein include, for example, aluminum carbonate, aluminum hydroxide, aluminum phosphate, aluminum hydroxycarbonate, dihydroxy aluminum sodium carbonate, aluminum magnesium glycinate, dihydroxy aluminum amino acetate, dihydroxy aluminum aminoacetic acid, calcium carbonate, calcium phosphate, aluminum magnesium hydrated sulfates, magnesium aluminate, magnesium alumino silicates, magnesium carbonate, magnesium glycinate, magnesium hydroxide, magnesium oxide, magnesium trisilicate, and mixtures thereof. Aluminum magnesium hydroxide sulfate (also known as magaldrate) is a preferred metallic antacid salt useful herein.

Optional Components

The compositions of this invention may also contain pharmaceutically-acceptable optional components which modify the physical and/or therapeutic effects of the composition. Such optional components may include, for example, emulsifiers, binders, lubricants, glidants, colorants, flavors and sweeteners. Such components are generally described in Marshall, "Solid Oral Dosage Forms", *Modern Pharmaceutics*, Volume 7, (Banker and Rhodes, editors), 359-427 (1979), incorporated by reference herein, and W. Gunsel, et al., "Tablets", *The Theory and Practice of Industrial Pharmacy* (L. Lachman, et al., editors, 2 ed.), 321-358 (1976), incorporated by reference herein.

Pharmaceutically-acceptable oils may be included to obtain a desired measured viscosity (as discussed below), preferably at levels of from about 0.1% to about 2%, more preferably from about 0.1% to about 1%. Such materials include, for example, vegetable oils, mineral oils and mixtures thereof. Certain emulsification materials, discussed above, may also be oils. However, as also discussed below, it is preferred that the levels of oils and other liquid materials in these compositions be minimized.

As will be appreciated by those skilled in the art, the lipid base material of the present composition may be present in any of a number of crystal forms, or polymorphs, depending upon the particular lipid material used. For compositions wherein POP fat is utilized as the lipid base material, it is preferred that the fat be present in the beta-prime-2 or beta-3 polymorph state. The crystal structure of the lipid base material useful herein may be affected by a variety of factors, as can be ascertained by one of skill in the art. Such factors include the presence of solids in the composition, the presence of emulsifiers, the processing conditions (particularly cooling temperatures and rates), and the particular lipid base material employed.

A preferred optional component in molded tablets of this invention (i.e., compositions that are formed upon solidification of a heated liquid composition after pouring into a suitable mold) is a "tempering aid". Such materials aid in the formation of a desired crystal structure for the lipid components of the present composition, such that the composition has a desired uniform, smooth, non-gritty texture and appearance. Tempering aids are preferably included at a level of from about 0.2% to about 2%. Among tempering aids useful herein are mixtures of mono- and diglycerides, such as Dur-Em 127 (manufactured by Durkee Foods, Division of SCM Corporation) and triglyceride mixtures, such as Cessa 60 (manufactured by Friwessa).

Also preferably, the compositions of this invention contain less than about 1% of materials that are liquid at ambient conditions in addition to any liquid components of the lipid material. It has been found that the level of such liquid materials may affect the storage stability of these compositions. More preferably these compositions contain less than about 0.5% of such additional liquid materials.

Other preferred optional components useful herein include flavorants and sweeteners, at levels of from about 0.01% to about 1.0%. Colorants may be included at typical levels of from about 0.01% to about 0.5%.

As stated above, the present compositions may be coated, to provide a coated unit dosage form. The coated compositions of the invention comprise a lipid-containing composition of this invention, covered with from about 10% to about 50%, preferably from about 10% to about 30%, (by weight of final coated composition) of a solid, water-soluble coating material having a melting point greater than about 45° C. Such coated compositions preferably are in unit-dosage form, i.e., containing an amount of pharmaceutical active material suitable for administration to a human subject, in one dose, according to good medical practice. The coated compositions of this invention preferably contain from about 0.5 to about 2.5 grams, preferably from about 1.0 to about 2.0 grams, of the lipid-containing composition of this invention.

Coating materials, and methods, among those useful herein are well known in the pharmaceutical arts. See, for example, W. Gunsel, et al., "Tablets", *The Theory and Practice of Industrial Pharmacy* (L. Lachman, et al., editors, 2d ed.) 321-358 (1976), incorporated by reference herein. Preferred coatings and materials are described in U.S. patent application Ser. No. 916,066, filed Oct. 6, 1986, incorporated by reference herein.

Methods

The chewable tablet compositions of this invention may be made by molding techniques. Molding techniques generally involve admixture of components in an essentially liquid form, followed by pouring into a desired tablet mold and cooling to a solid, or semi-solid form. The compositions of this invention are preferably in molded form.

The lipid base material used in molded compositions of the present invention is preferably in a stable crystal form, such that the composition is comprised of stable crystals less than about 5 microns, preferably from about 1 to about 2 microns, in size, and the composition has a uniform, smooth, non-gritty appearance and rheology. Such parameters, and the factors which influence them, are analagous to parameters that are well known in the chocolate confectionery arts. As discussed above, materials may be added to the present compositions which aid in obtaining a preferred, stable crystal structure, or "temper". Processing conditions for making molded compositions are also critical, and are preferably controlled to yield a preferred tempered composition. Such "tempering", for compositions utilizing POP fat as a lipid base material, typically involves cooling of the product in liquid form, to a temperature of approximately 22° C. This cooling induces formation of a variety of crystals of different melting points. The composition is then heated, with stirring, to approximately 29.5° C., melting the undesired lower-melting crystals. (The fluid product at this point is thereby "seeded" with higher-melting crystals.) The fluid product is then poured into molds, vibrated to remove air bubbles, and slowly cooled to solidify the composition into a product having the desired crystal form.

The molded, uncoated compositions of this invention preferably have a viscosity (herein "measured viscosity") of less than about 10,000 centipoises (cps), while in liquid mixture (melted) at approximately 40° C. More preferably, the measured viscosity is less than about 8,000 cps, more preferably less than about 5,000 cps. This measured viscosity may be measured using a Brookfield Viscometer, Model RVT/2 with Helipath (Spindle C, at 10 rpm). The uncoated product is first melted, using a water bath, at a temperature of approximately 50° C. The product is then mixed for approximately one hour, using a paddle mixer (such as a Model K4553 Kitchen Aid Mixer, at speed setting #2). The product mixture is cooled slowly (over a period of approximately 30 minutes), while mixing, to a temperature of approximately 40° C. The mixing is stopped, and the viscometer spindle is then inserted into the product mass. The viscosity reading is taken at equilibrium, or after lapse of 30 seconds, whichever comes first.

The product measured viscosity may be obtained by selection of materials and processing conditions. For example, the desired measured viscosity may be obtained by selection of the type and level of lipid material, emulsifiers, particulate materials (active material and dispersant material) and optional materials. The measured viscosity of the present compositions may be obtained by control of processing conditions, including (for example) milling of materials, order of addition of materials, and tempering conditions.

In particular, the particle size of particulate materials of the present compositions are controlled by selection of materials and/or by selection of processing conditions. (As used herein "particulate materials" include the pharmaceutical active material, dispersant material, and any optional components that are not substantially soluble in the lipid material or other components of the composition.) The mean (by volume) particle size of the particulate materials is in the range of from about 4 microns to about 10 microns, preferably from about 6 microns to about 10 microns. Less than about 10% of the particulate materials have a particle size greater than about 30 microns. (As used herein, "particle size" of a particulate refers to the diameter of a sphere having a volume equal to that of said particulate.)

The particle size of the uncoated compositions of this invention may be determined using a Malvern 2600/3600 Particle Sizer (manufactured by Malvern Instrument Company). The uncoated composition is melted in mineral oil, at approximately 40° C. The mixture is then dispersed using a high speed mixer, for at least about 5 minutes. After mixing, several drops of the product mixture are placed in the Particle Sizer, using mineral oil as the dispersant. The product mixture is mixed in the apparatus at a medium speed setting.

The following non-limiting Examples illustrate the compositions, processes and uses of the present invention.

EXAMPLE I

A coated antacid composition according to this invention was made comprising:

| Component | % Bulk Composition | % Final Tablet |
|---|---|---|
| POP fat[1] | 34.009 | 28.908 |
| sucrose | 31.640 | 26.894 |
| magaldrate[2] | 31.640 | 26.894 |
| simethicone | 0.991 | 0.842 |
| Span 80[3] | 0.478 | 0.406 |
| Tween 60[4] | 0.148 | 0.126 |
| sucrose monoester[5] | 0.487 | 0.414 |
| sodium stearoyl lactylate[6] | 0.009 | 0.008 |
| Dur-Em 127[7] | 0.498 | 0.423 |
| peppermint oil | 0.100 | 0.085 |
| | 100.000 | |
| (Coating) | | |
| Neosorb P100T[8] | | 8.700 |
| Iycasin | | 4.100 |
| mannitol | | 2.200 |
| | | 100.000 |

[1]lipid base material, comprising approximately 88% SUS triglyceride, with an St:P ratio of approximately 0.13
[2]aluminum magnesium hydroxide sulfate, antacid active material
[3]sorbitan molooleate emulsifier, HLB = 4.3, manufactured by ICI Americas, Inc.
[4]polyoxyethylene (20) sorbitan monooleate emulsifier, HLB = 14.9, manufactured by ICI Americas, Inc.
[5]emulsifier, HLB = 15.0
[6]emulsifier, HLB = 9.0
[7]tempering aid mixture of mono- and diglycerides, HLB = 2.8, manufactured by Durkee Foods, Division of SCM Corporation.
[8]fine sorbitol powder, manufactured by The Roquette Corporation A composition according to this invention was made by admixing the magaldrate and sugar, and heating to approximately 40° C. Separately, approximately 55% of the POP fat was melted at approximately 40° C., and approximately 10% of the Span 80 was added, and mixed. The POP-fat mixture was then added to the active/sugar mixture, maintaining the temperatures at approximately 40° C., and mixed for approximately 45 minutes. The mixture was passed through a 4-roll roller mill, at approximately 300 psi, to ensure adequate contact and mixture of the lipid base material and the powdered materials. The 4 mill rollers were at temperatures of approximately 27° C., 21° C., 21° C. and 21° C., respectively.

Separately, the remaining portion of POP (approximately 45% of the original quantity) was admixed with the remaining portion of Span 80 (approximately 90% of the original quantity), the Dur-Em, and the sodium stearyl lactylate emulsifier, for approximately 10 minutes, at a temperature of approximately 50° C. The sucrose monoester and Tween 60 were dissolved in ethanol, and then added to the composition. The peppermint oil and simethicone were then added, and the compositions mixed for approximately 45 minutes, maintaining the temperature at approximately 50° C. The milled POP mixture was then added to this POP-/emulsifier mixture, and mixed for approximately 15 minutes.

The composition was then cooled to approximately 22° C., and tempered by rapidly raising the temperature to approximately 29.5° C., forming seed crystals. The composition was then poured into tablet molds and allowed to solidify. The average tablet weight was approximately 2.2 g.

The tablets were then coated by placing them in a conventional coating pan apparatus. A portion of the lycasin was added, and the tablets evenly wetted. The mannitol was then added, and the tablets mixed for approximately 10 minutes, and then dried for approximately one hour. The tablets were then coated with lycasin and Neosorb, following the same procedure, and dried for approximately 12 hours.

A coated antacid tablet, comprised as above, was administered to a human subject experiencing heartburn, and was effective in reducing the severity of symptoms. The average HLB of the lipid containing core composition of this Example is calculated to be approximately 8.1. The measured viscosity of the lipid-containing core composition is found to be approximately 6,600 cps.

EXAMPLE II

A coated antacid composition according to this invention is made comprising:

| Component | % Bulk Composition | % Final Tablet |
|---|---|---|
| POP fat | 28.0 | 23.80 |
| sucrose | 15.0 | 12.75 |
| sorbitol | 15.0 | 12.75 |
| calcium carbonate | 40.0 | 34.00 |
| sucrose monoester | 1.0 | 0.85 |
| Tween 60 | 0.5 | 0.43 |
| flavorant | 0.5 | 0.42 |
|  | 100.00 |  |
| (Coating) |  |  |
| sorbitol |  | 3.00 |
| corn syrup |  | 1.00 |
| sucrose |  | 10.50 |
| maltrin |  | 0.50 |
|  |  | 100.00 |

A coated antacid composition, comprised as above, is made by a method analogous to that described in Example I. The tablets are formed into unit dosage tablets, containing approximately 2.2 grams of the lipid-containing composition. The average HLB of the lipid-containing core composition of this Example is calculated to be approximately 14.9.

EXAMPLE III

A coated antacid composition according to this invention was made comprising:

| Component | % Bulk Composition | % Final Tablet |
|---|---|---|
| POP fat | 35.942 | 30.000 |
| sucrose | 26.119 | 21.800 |
| magaldrate | 35.703 | 29.800 |
| Cessa 60[1] | 0.994 | 0.830 |
| Myrj 52[2] | 0.503 | 0.402 |
| Caprol PGE 860[3] | 0.395 | 0.330 |
| Polyaldo HGDS[4] | 0.252 | 0.210 |
| flavorant | 0.092 | 0.077 |
|  | 100.000 |  |

| Component | % Bulk Composition | % Final Tablet |
|---|---|---|
| (Coating) |  |  |
| sorbitol solution[5] |  | 10.700 |
| lycasin |  | 1.060 |
| mannitol |  | 4.023 |
| Klucel EF[6] |  | 0.750 |
|  |  | 100.000 |

[1] triglyceride mixture, tempering aid, manufactured by Friwessa
[2] polyoxyl (40) stearate, nonionic emulsifier, HLB = 16.9, manufactured by ICI Americas, Inc.
[3] decaglycerol mono-dioleate nonionic emulsifier, HLB = 11.0, manufactured by Capital City Products Co., division of Stokely-Van Camp, Inc.
[4] hexaglycerol distearate nonionic emulsifier, HLB = 7.0, manufactured by Glyco, Inc.
[5] 70% solution
[6] hydroxypropyl cellulose gum, manufactured by Hercules Chemical Company.

A coated composition, comprised as above, was made by a method analogous to that described in Example I.

EXAMPLE IV

An uncoated composition according to this invention is made comprising:

| Component | % by Weight |
|---|---|
| Hydrokote SP1 fat* | 34.00 |
| vegetable oil | 1.50 |
| sucrose | 30.93 |
| magaldrate | 30.93 |
| simethicone | 1.00 |
| Caprol PGE 860 | 0.90 |
| sucrose monoester | 0.50 |
| Tween 60 | 0.10 |
| Span 80 | 0.04 |
| flavorant | 0.10 |

*lauric lipid material, manufactured by Capital City Products Co.

EXAMPLE V

An uncoated composition according to this invention is made comprising:

| Component | % by Weight |
|---|---|
| POP fat | 35.00 |
| mannitol | 15.76 |
| bismuth subsalicylate | 25.95 |
| calcium carbonate | 20.00 |
| hexaglycerol distearate | 0.25 |
| polyoxyl (40) stearate | 0.50 |
| sucrose monoester | 0.48 |
| flavorant | 1.60 |
| sweetener | 0.20 |
| colorant | 0.26 |

Unit dosage tablets, comprised as above, are made containing approximately 1.1 grams of composition per tablet. Two tablets are administered to a human subject experiencing nausea, lessening the severity of symptoms. The average HLB of the composition of this Example is calculated to be approximately 14.6.

What is claimed is:

1. A molded pharmaceutical composition, comprising:
   (a) from about 10% to about 50% of a lipid material having a melting point of from about 26° C. to about 37° C.;
   (b) from about 10% to about 50% of a particulate dispersant material;
   (c) from about 0.1% to about 3% of an emulsifier; and (d) a safe and effective amount of a pharmaceutical active material;

wherein the pharmaceutical materials in said composition have a mean particle size of from about 4 microns to about 10 microns, with less than about 10% of said particulates greater than about 30 microns in size, and wherein further the measured viscosity of said composition is less than about 10,000 cps at about 40° C.

2. A molded pharmaceutical composition according to claim 1, wherein the particulate materials in said composition have a mean particle size of from about 6 microns to about 10 microns.

3. A molded pharmaceutical composition according to claim 1, having a measured viscosity less than about 5000 cps at about 40° C.

4. A molded pharmaceutical composition according to claim 1, wherein said lipid material has a melting point of from about 32° C. to about 35° C.

5. A molded pharmaceutical composition according to claim 4, wherein said lipid material melts sharply at about 33° C.

6. A molded pharmaceutical composition according to claim 4, wherein said lipid base material is present at a level of from about 25% to about 40%.

7. A molded pharmaceutical composition according to claim 6, wherein said particulate dispersant material is present at a level of from about 20% to about 35%.

8. A molded pharmaceutical composition according to claim 7, containing a low HLB emulsifier.

9. A molded pharmaceutical composition according to claim 8, wherein said low HLB emulsifier is present at a level of from about 0.1% to about 1%.

10. A molded pharmaceutical composition according to claim 1, additionally comprising from about 0.1% to about 1% of an oil.

11. A molded pharmaceutical composition according to claim 1, additionally comprising a tempering aid.

12. A molded pharmaceutical composition according to claim 11, containing less than about 1% of liquid materials.

13. A molded pharmaceutical composition according to claim 11, wherein said pharmaceutical active material is useful in the treatment of gastrointestinal disorders.

14. A molded pharmaceutical composition according to claim 13, wherein said pharmaceutical active material is a metallic antacid salt.

15. A molded pharmaceutical composition according to claim 13, wherein said pharmaceutical active material is a bismuth salt.

16. A coated pharmaceutical composition, in unit dosage form, comprising from about 50% to about 90% of a composition according to claim 1, and from about 10% to about 50% of a coating material.

* * * * *